(12) United States Patent
Romanauskas et al.

(10) Patent No.: US 6,723,238 B2
(45) Date of Patent: Apr. 20, 2004

(54) BLOOD CENTRIFUGE CUP HAVING A REPLACEABLE COMPARTMENT FOR FILTER SUPPORT

(75) Inventors: William Andrew Romanauskas, Southbury, CT (US); Edward Thomas Sheeran, Jr., Southbury, CT (US)

(73) Assignee: Kendro Laboratory Products, L.P., Newton, CT (US)

( * ) Notice: Subject to any disclaimer, the term of this patent is extended or adjusted under 35 U.S.C. 154(b) by 132 days.

(21) Appl. No.: 09/956,603

(22) Filed: Sep. 19, 2001

(65) Prior Publication Data
US 2002/0046967 A1 Apr. 25, 2002

Related U.S. Application Data

(60) Provisional application No. 60/233,975, filed on Sep. 20, 2000.

(51) Int. Cl.[7] .................. B01D 21/26; B01D 35/00; B01D 35/02; B04B 7/08
(52) U.S. Cl. ............... 210/232; 210/257.1; 210/435; 422/102; 422/104; 494/36; 494/43; 604/408
(58) Field of Search .......................... 210/232, 257.1, 210/360.1, 435; 422/102, 104; 494/16, 36, 43; 604/408, 410

(56) References Cited

U.S. PATENT DOCUMENTS

| | | | | |
|---|---|---|---|---|
| 4,874,582 A | * | 10/1989 | Gordon et al. | 422/102 |
| 5,092,996 A | * | 3/1992 | Spielberg | 210/232 |
| 5,100,564 A | * | 3/1992 | Pall et al. | 210/782 |
| 5,547,591 A | * | 8/1996 | Hagihara et al. | 210/782 |
| 6,053,885 A | * | 4/2000 | Beshel | 604/4 |

FOREIGN PATENT DOCUMENTS

JP  9-47688  * 2/1997

OTHER PUBLICATIONS

Derwent abstract of Japanese Patent Application No. 9-47688 (1999).*

* cited by examiner

Primary Examiner—John Kim
(74) Attorney, Agent, or Firm—Baker & Hostetler LLP

(57) ABSTRACT

A centrifuge bucket, for holding a first article, further comprises a compartment for holding a second article, and an arrangement for securing the compartment to an outer surface of the centrifuge bucket.

6 Claims, 4 Drawing Sheets

BLOOD CENTRIFUGE CUP HAVING A REPLACEABLE COMPARTMENT FOR FILTER SUPPORT

The present application is claiming priority of U.S. Provisional patent application Ser. No. 60/233,975, filed on Sep. 20, 2000.

FIELD OF THE INVENTION

In the production of leukocyte reduced red blood cells, plasma and platelet components, a blood bag set that includes a filled donor bag, a component bag for each blood product, and one or more leukocyte removal filter(s) connected together by tubing, is spun in a centrifuge. The present invention provides a means for a user to consistently load this blood bag set into a centrifuge bucket, resulting in high quality blood component products.

BACKGROUND OF THE INVENTION

After a donor blood bag is filled with whole blood drawn from a donor, the blood bag is spun in a centrifuge to separate the whole blood into components of red cells, plasma, and platelets. In addition to the donor blood bag, a red blood cell bag, a plasma bag and a platelet bag are attached to the donor blood bag with tubing to make a blood bag set. The red blood cell bag, a plasma bag and a platelet bag are also known as satellite bags.

In a conventional centrifuge system, the blood bag set is either placed directly into a centrifuge bucket or into an adapter that is then placed into the bucket. A user literally stuffs the blood bag set into the bucket or adapter. The placement of the blood bag set into the centrifuge bucket or adapter may affect the separation consistency and the quality of the blood components.

The bucket has pockets that are machined, molded, injection molded or formed so that the bucket is pivotable about pins disposed about a rotor body. At rest the bucket orientation is vertical but when the rotor is rotated about its axis the bucket swings outward to a horizontal position relative to the axis of the rotor. This horizontal orientation allows for a more distinct separation of blood components.

Recently, blood bag manufacturers introduced leukocyte removal filters to the blood bag sets to improve quality of blood products. These blood bag sets with filters must be centrifuged. In addition to the added volume, the filters must be adequately supported to prevent damage to the filter(s) during centrifugation. The filters must also be loaded into the centrifuge bucket so as not to damage the donor bag or any of the satellite bags. Several prior art systems have attempted to minimize the potential damage to the filters.

U.S. Pat. No. 5,092,996 to Spielberg, describes a blood filtering system that includes a filter having a support to hold the filter in place on top of a blood bag centrifuge bucket. This system suffers from several deficiencies. The size of the filter that can be accommodated is dictated by the diameter of the bucket, the system does not appear to be capable of accommodating multiple filters, and the internal volume of the bucket cavity that is available for the blood bag is reduced when the support is present.

U.S. Pat. No. 5,100,564 to Pallet al. describes a blood collecting and processing system in which filter assemblies are retained by a bracket. The bracket is configured to fit into a centrifuge bucket to protect the filters. Disadvantageously, the bracket appears to be capable of retaining only a filter for which the bracket is particularly designed. Furthermore this arrangement also reduces the internal volume of the bucket cavity, thus reducing the volume available for a blood bag.

U.S. Pat. No. 5,547,591 to Hagihara et al. describes a system in which a filter is placed outside of a centrifuge bucket and secured relative to the rotor. The deficiencies of this approach are that the filters are inconvenient to install because they must be secured to the rotor body, and the tubing between the filter and a blood bag may interfere with the swinging of the centrifuge bucket. This arrangement of the tubing may prevent the bucket from swinging to its fully horizontal position, or the tubing may get caught between the bucket and the rotor body to prevent the bucket from properly returning to its vertical position. The interference with the movement of the bucket also adversely impacts the quality of the blood components.

The deficiencies of the systems described above are overcome by the present invention.

SUMMARY OF INVENTION

A centrifuge bucket in accordance with the present invention is for holding a first article, and further comprises a compartment for holding a second article, and a means for securing the compartment to an outer surface of the centrifuge bucket. The securing means can be, for example, a groove for accommodating a lip situated along an edge of the compartment.

A compartment attached to a centrifuge swinging bucket holds one or blood component filters of a blood bag set. The compartment securely houses the filter(s) and segregates the filter(s) from other parts of the blood bag set. This eliminates potential damage to the filter and potential damage caused by the filter to any of the bags in the blood bag set. Moreover, the compartment is outside the bucket cavity envelope, thus increasing the usable volume of the bucket cavity. A centrifuge manufacturer, rather than making a centrifuge bucket dedicated for use with a particular filter, can adapt a less costly filter compartment to the centrifuge bucket to accommodate filters of various shapes.

DETAILED DESCRIPTION OF THE PREFERRED EMBODIMENTS

Figure 1:
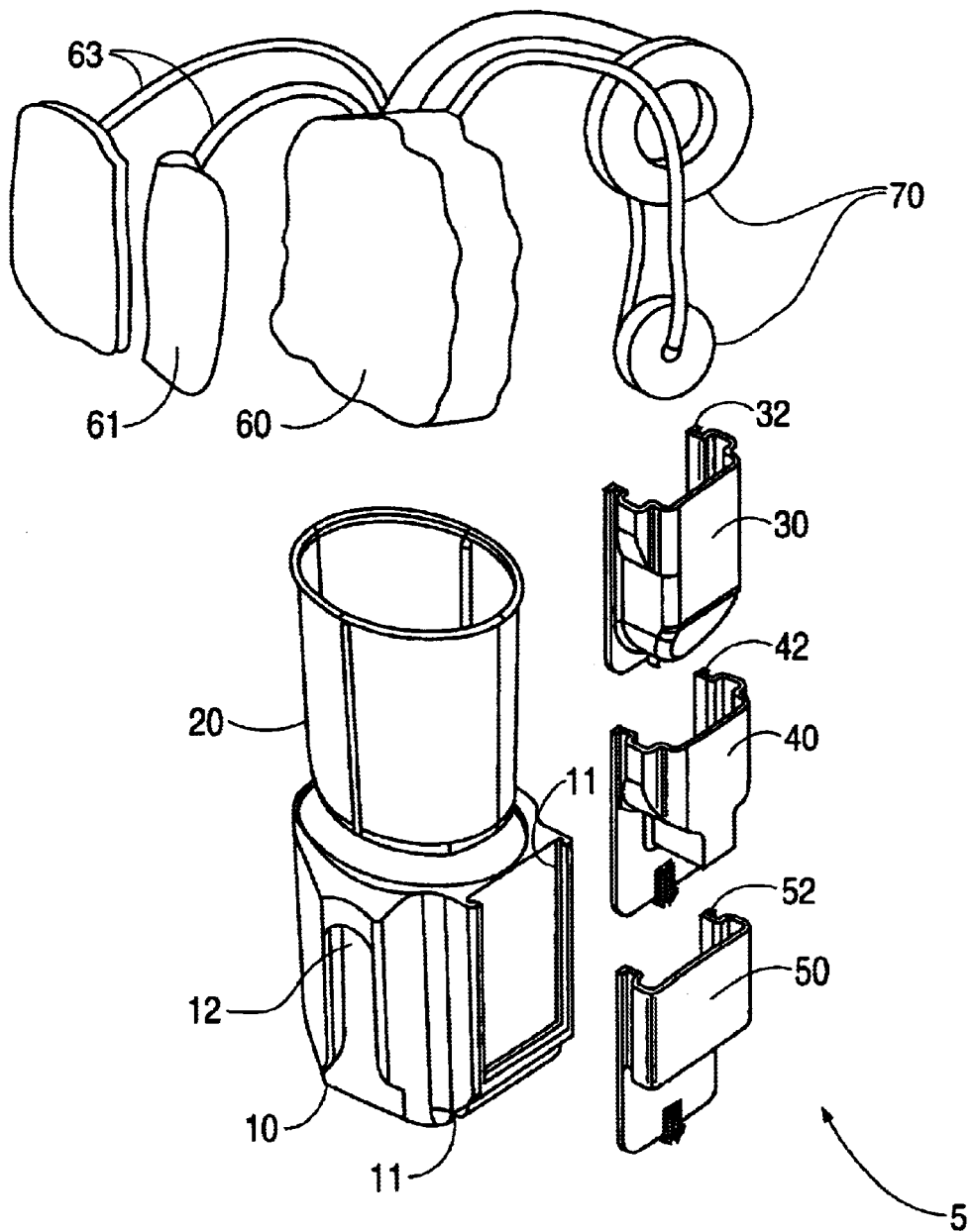
FIG. 1 is an exploded pictorial isometric of a centrifuge bucket system that includes a centrifuge bucket and a blood bag adapter in accordance with the present invention.

The present invention can best be described by reference to the figures, where FIG. 1 is an exploded pictorial isometric of a centrifuge bucket system 5 that includes a centrifuge bucket 10 and a blood bag adapter 20. Centrifuge bucket system 5 also includes a filter compartment, of which three variations are shown in FIG. 1, namely, a first variation filter compartment 30, a second variation filter compartment 40, and a third variation filter compartment 50. The various filter compartments 30, 40 and 50 are provided to hold filters of different sizes or shapes, as would typically be found from different filter manufacturers.

During operation, system 5 holds one of the filter compartments 30, 40 or 50. Each of filter compartments 30, 40 and 50 has a lip 32, 42, and 52, respectively, situated along a peripheral edge. Centrifuge bucket 10 has a groove 11 into 30 which any of lips 32, 42 or 52 can slide. Groove 11 thus engages any of lips 32, 42 or 52 and secures the respective compartment to an outer surface, for example, a wall, of centrifuge bucket 10. Groove 11 interchangeably accommodates lips 32, 42 and 52, and thus permits removal and reattachment of any of compartments 30, 40, or 50.

Figure 2:
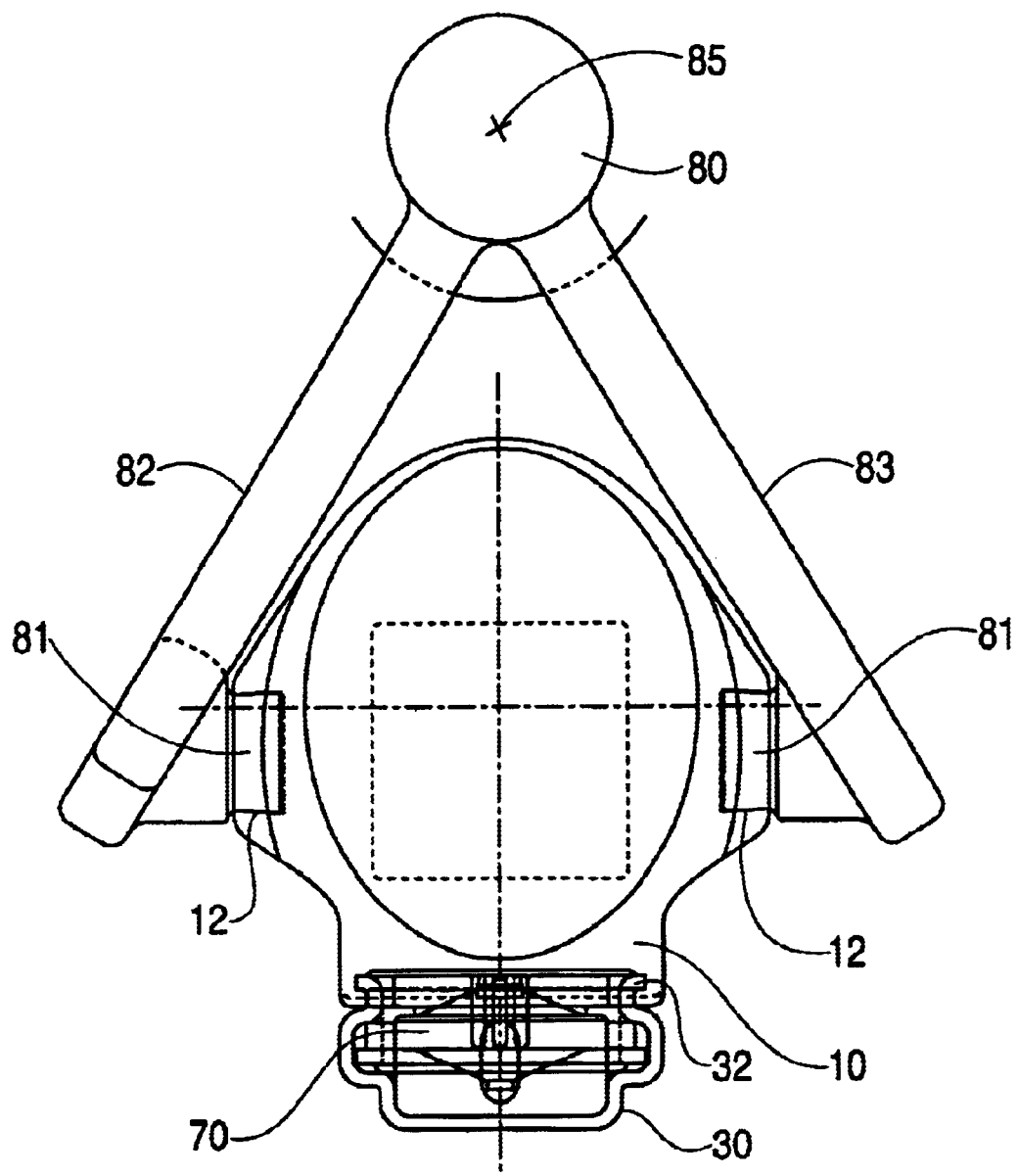
FIG. 2 is a top plan view of a centrifuge bucket in accordance with the present invention, mounted on a rotor body of a rotor and vertically oriented, parallel to an axis of rotation of the rotor.

Centrifuge bucket 10 also has a pocket 12 on each side that allows it to be disposed about a pair of pins 81 (FIG. 2) of a rotor body 80 (FIG. 2). The open pockets 12 also allow centrifuge bucket 10 to be readily removed from rotor body 80.

A donor blood bag 60, one or more satellite bags 61, and connecting tubing 63 are placed inside a blood bag adapter 20. The blood bag adapter 20 with its contents is then placed inside a cavity in centrifuge bucket 10. One or more filter(s) 70 are placed into the filter compartment 30, 40, or 50. In operation, when rotor body 80 is rotated about an axis of rotation 85, centrifuge bucket 10 pivots about rotor body pins 81 allowing centrifuge bucket 10 to swing out to a horizontal position relative to the axis of rotation 85.

FIG. 2 is a top plan view of a centrifuge bucket in accordance with the present invention. FIG. 2 shows two rotor arms 82, 83 of a rotor body 80, a pair of rotor body pins 81, centrifuge bucket 10, filter compartment 30, and filter 70. Centrifuge bucket 10, and filter compartment 30, which contains filter 70, are shown in their vertical positions, substantially parallel to an axis of rotation 85 of rotor body 80.

Figure 3:
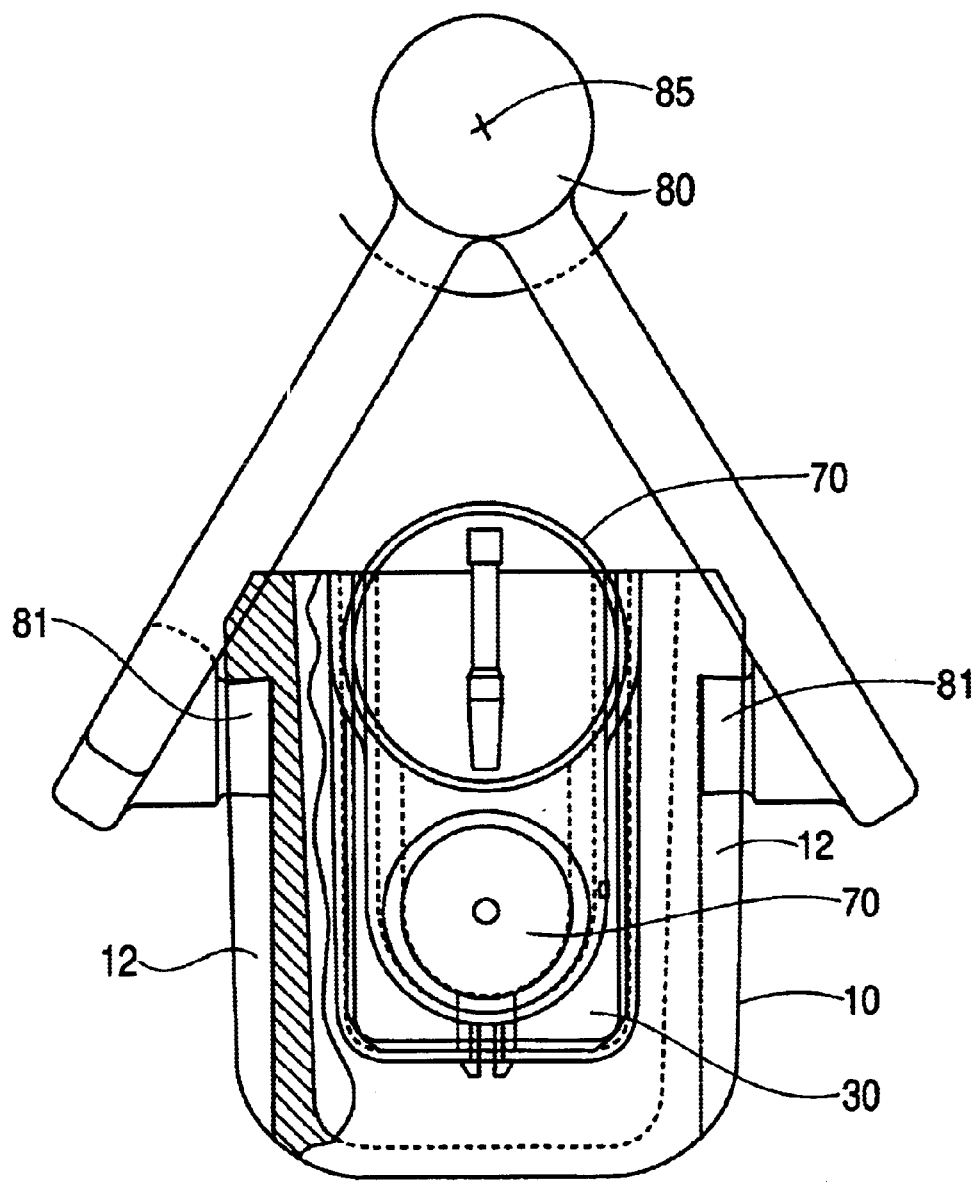
FIG. 3 is a top plan view of the centrifuge bucket of FIG. 2 horizontally oriented relative to the axis of the rotor.

FIG. 3 is a top plan view showing bucket 10, filter compartment 30, and filter 70 in a horizontal position, substantially perpendicular to axis 85, during centrifugation. Pockets 12 of centrifuge bucket 10 are rotatably disposed between the pair of rotor body pins 81 such that centrifuge bucket 10 may swing between the vertical position shown in FIG. 2, to the horizontal position shown in FIG. 3.

Figure 4:
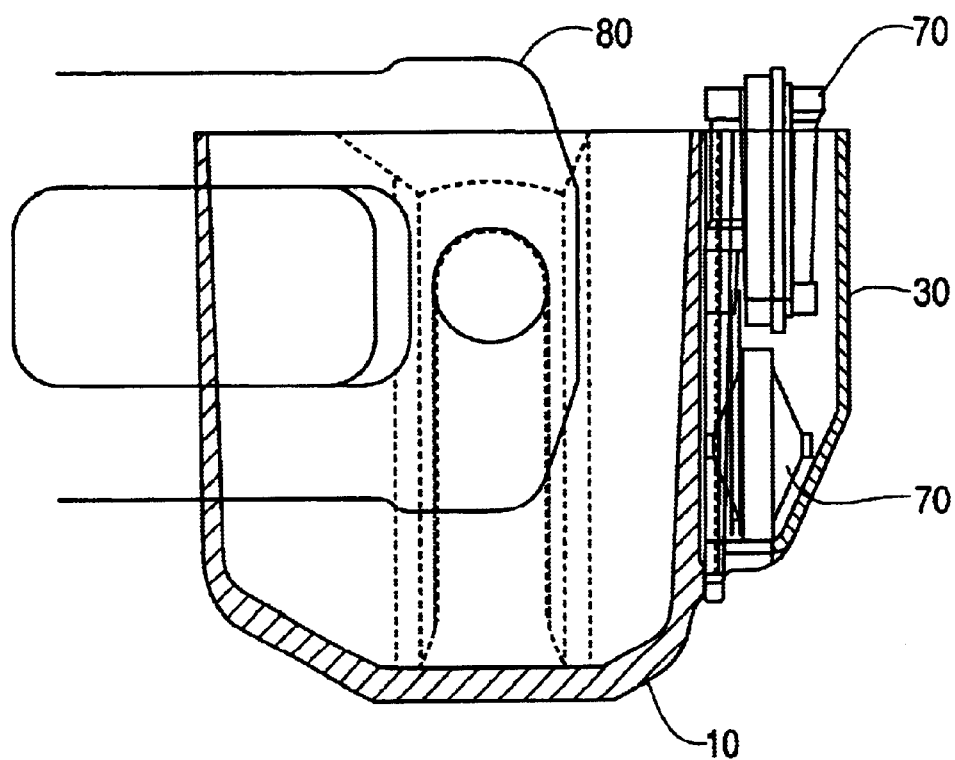
FIG. 4 is a front elevation view of the centrifuge bucket of FIG. 2, in vertical section and shown in the vertical position, at rest.

FIG. 4 is a front elevation view with bucket 10 and filter compartment 30 in vertical section with filters 70 in place. Bucket 10, filter compartment 30, and two filters 70 are shown in the vertical position, at rest, with respect to rotor body 80.

Those skilled in the art, having the benefit of the teachings of the present invention may impart numerous modifications thereto. Such modifications are to be construed as lying within the scope of the present invention, as defined by the appended claims.

What is claimed is:

1. A centrifuge bucket for holding a first article, said centrifuge bucket further comprising:

a compartment for holding a second article; and means for securing said compartment to an outer surface of said centrifuge bucket wherein said securing means comprises a groove for accommodating a lip situated along an edge of said compartment.

2. The centrifuge system of claim 1, wherein said first article is a blood bag.

3. The centrifuge system of claim 1, wherein said second article is a blood component filter.

4. The centrifuge bucket of claim 1, wherein said second article is a leukocyte removal filter.

5. The centrifuge bucket of claim 1, wherein said securing means permits removal and reattachment of said compartment from said centrifuge bucket.

6. The centrifuge bucket of claim 1, wherein said compartment is one of a plurality of compartments, each having a different physical configuration, and wherein said securing means can interchangeably accommodate each of said plurality of compartments.

* * * * *

UNITED STATES PATENT AND TRADEMARK OFFICE
CERTIFICATE OF CORRECTION

PATENT NO. : 6,723,238 B2
DATED : April 20, 2004
INVENTOR(S) : Romanauskas et al.

It is certified that error appears in the above-identified patent and that said Letters Patent is hereby corrected as shown below:

Title page,
Item [73], Assignee address should read -- Newtown, CT (US) --.

Signed and Sealed this

Ninth Day of November, 2004

JON W. DUDAS
*Director of the United States Patent and Trademark Office*